United States Patent
Yoon et al.

(10) Patent No.: US 9,603,909 B2
(45) Date of Patent: Mar. 28, 2017

(54) COMPOSITION CAPABLE OF IMPROVING STABILITY OF BACTERIOPHAGE LYSIN PROTEINS

(75) Inventors: Seong Jun Yoon, Seoul (KR); Soo Youn Jun, Seoul (KR); Gi Mo Jung, Seoul (KR); Sang Hyeon Kang, Seoul (KR)

(73) Assignee: Intron Biotechnology, Inc. (KR)

( * ) Notice: Subject to any disclaimer, the term of this patent is extended or adjusted under 35 U.S.C. 154(b) by 0 days.

(21) Appl. No.: 14/404,158

(22) PCT Filed: May 29, 2012

(86) PCT No.: PCT/KR2012/004204
§ 371 (c)(1),
(2), (4) Date: Dec. 1, 2014

(87) PCT Pub. No.: WO2013/180316
PCT Pub. Date: Dec. 5, 2013

(65) Prior Publication Data
US 2015/0224179 A1 Aug. 13, 2015

(51) Int. Cl.
| A61K 9/08 | (2006.01) |
| A61K 39/395 | (2006.01) |
| A61K 38/47 | (2006.01) |
| A61K 38/16 | (2006.01) |
| A61K 47/02 | (2006.01) |
| A61K 47/34 | (2017.01) |
| C12N 7/00 | (2006.01) |

(52) U.S. Cl.
CPC ............ *A61K 38/47* (2013.01); *A61K 38/162* (2013.01); *A61K 47/02* (2013.01); *A61K 47/34* (2013.01); *C12N 7/00* (2013.01); *C12N 2795/10122* (2013.01); *C12N 2795/10151* (2013.01); *C12Y 302/01017* (2013.01)

(58) Field of Classification Search
CPC .................. A61K 9/08; A61K 39/395
USPC .......................................... 514/12.1
See application file for complete search history.

(56) References Cited

U.S. PATENT DOCUMENTS

| 2006/0159653 A1 | 7/2006 | Saito et al. |
| 2009/0264629 A1 | 10/2009 | Saito et al. |
| 2010/0254950 A1* | 10/2010 | Yoon ............... A01N 63/00 424/93.6 |

FOREIGN PATENT DOCUMENTS

WO    WO 2004/045645 A2    6/2004

OTHER PUBLICATIONS

Soo Youn Jun et al., "Antibacterial Properties of a Pre-Formulated Recombinant Phage Endolysin, SAL-1," *Int'l Journal of Antimicrobial Agents* 41, pp. 156-161 (Elsevier 2012).
Soo Youn Jun et al., "Comparison of the Antibacterial Properties of Phage Endolysins, SAL-1 and LysK," *Antimicrobial Agents and Chemotherapy*, vol. 55, No. 4, pp. 1764-1767 (American Society for Microbiology Jan. 24, 2011).
Mathias Schmelcher et al., "*Listeria* Bacteriophage Peptidoglycan Hydrolases Feature High Thermoresistance and Reveal Increased Activity After Divalent Metal Cation Substitution," *Appl Microbial Biotechnol* 93; pp. 633-643 (Springer-Verlag Jul. 1, 2011).
Feb. 26, 2013 International Search Report for PCT/KR2012/004204.

* cited by examiner

*Primary Examiner* — Maryam Monshipouri
(74) *Attorney, Agent, or Firm* — Husch Blackwell LLP

(57) ABSTRACT

The present invention relates to a composition for improving the stability of bacteriophage originated lysin proteins greatly even when the composition contains the bacteriophage originated lysin proteins at a high concentration. More precisely, the present invention relates to a method and a composition for improving significantly the stability of SAL-1 or LysK, the bacteriophage originated lysin protein, included at a high concentration in the composition.

14 Claims, 4 Drawing Sheets

Cell Disruption
- Lysis buffer : 50mM Na2HPO4, pH 7.5, 10mM EDTA, 1mM DTT
- Cell resuspension 10 mL Lysis buffer / 1 g wet cell
- Cell disruption
- Centrifugation: Recovery of soluble protein

SP FF Chromatography
- Buffer A : 25mM Na2HPO4, pH 7.5, 10mM EDTA
- Buffer B : 25mM Na2HPO4, pH 7.5, 10mM EDTA with 1M NaCl
- Buffer C : 25mM Na2HPO4, pH 7.5, 10mM EDTA, 50mM NaCl with 0.5% Triton X-100
- Apply sample->2CV in buffer A -> 30CV in buffer C -> 20CV in buffer A -> 5 CV in 25% buffer B -> Elution by gradient (20CV in 25-100% buffer B)

Toyopearl PPG-600M Chromatography
- Buffer A : 25mM Na2HPO4, pH 7.5 with 1M NaCl
- Buffer B : 25mM Na2HPO4, pH 7.5 with 1M Urea
- Loading (purified by SP FF) ->4CV in 30% buffer B -> Elution by 100% buffer B

Fig. 1

Poloxamer Effect - SEC HPLC yield (%)

SEQUENCE LISTING

<160> NUMBER OF SEQ ID NOS: 2

<210> SEQ ID NO 1
<211> LENGTH: 495
<212> TYPE: PRT
<213> ORGANISM: Artificial Sequence
<220> FEATURE:
<223> OTHER INFORMATION: synthetic sequence

<400> SEQUENCE: 1

```
Met Ala Lys Thr Gln Ala Glu Ile Asn Lys Arg Leu Asp Ala Tyr Ala
1               5                   10                  15

Lys Gly Thr Val Asp Ser Pro Tyr Arg Ile Lys Lys Ala Thr Ser Tyr
            20                  25                  30

Asp Pro Ser Phe Gly Val Met Glu Ala Gly Ala Ile Asp Ala Asp Gly
        35                  40                  45

Tyr Tyr His Ala Gln Cys Gln Asp Leu Ile Thr Asp Tyr Val Leu Trp
    50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
```

|   |   |   | 100 |   |   |   | 105 |   |   |   | 110 |   |   |
|---|---|---|---|---|---|---|---|---|---|---|---|---|---|
| Gln | Gln | Trp | Gly | His | Ile | Gly | Ile | Val | Tyr | Asp | Gly | Gly | Asn | Thr | Ser |

Thr Phe Thr Ile Leu Glu Gln Asn Trp Asn Gly Tyr Ala Asn Lys Lys
115                 120                 125

Pro Thr Lys Arg Val Asp Asn Tyr Tyr Gly Leu Thr His Phe Ile Glu
130                 135                 140

Ile Pro Val Lys Ala Gly Thr Thr Val Lys Lys Glu Thr Ala Lys Lys
145                 150                 155                 160

Ser Ala Ser Lys Thr Pro Ala Pro Lys Lys Ala Thr Leu Lys Val
165                 170                 175

Ser Lys Asn His Ile Asn Tyr Thr Met Asp Lys Arg Gly Lys Lys Pro
180                 185                 190

Glu Gly Met Val Ile His Asn Asp Ala Gly Arg Ser Ser Gly Gln Gln
195                 200                 205

Tyr Glu Asn Ser Leu Ala Asn Ala Gly Tyr Ala Arg Tyr Ala Asn Gly
210                 215                 220

Ile Ala His Tyr Tyr Gly Ser Glu Gly Tyr Val Trp Glu Ala Ile Asp
225                 230                 235                 240

Ala Lys Asn Gln Ile Ala Trp His Thr Gly Asp Gly Thr Gly Ala Asn
245                 250                 255

Ser Gly Asn Phe Arg Phe Ala Gly Ile Glu Val Cys Gln Ser Met Ser
260                 265                 270

Ala Ser Asp Ala Gln Phe Leu Lys Asn Glu Gln Ala Val Phe Gln Phe
275                 280                 285

Thr Ala Glu Lys Phe Lys Glu Trp Gly Leu Thr Pro Asn Arg Lys Thr
290                 295                 300

Val Arg Leu His Met Glu Phe Val Pro Thr Ala Cys Pro His Arg Ser
305                 310                 315                 320

Met Val Leu His Thr Gly Phe Asn Pro Val Thr Gln Gly Arg Pro Ser
325                 330                 335

Gln Ala Ile Met Asn Lys Leu Lys Asp Tyr Phe Ile Lys Gln Ile Lys
340                 345                 350

Asn Tyr Met Asp Lys Gly Thr Ser Ser Ser Thr Val Val Lys Asp Gly
355                 360                 365

Lys Thr Ser Ser Ala Ser Thr Pro Ala Thr Arg Pro Val Thr Gly Ser
370                 375                 380

Trp Lys Lys Asn Gln Tyr Gly Thr Trp Tyr Lys Pro Glu Asn Ala Thr
385                 390                 395                 400

Phe Val Asn Gly Asn Gln Pro Ile Val Thr Arg Ile Gly Ser Pro Phe
405                 410                 415

Leu Asn Ala Pro Val Gly Gly Asn Leu Pro Ala Gly Ala Thr Ile Val
420                 425                 430

Tyr Asp Glu Val Cys Ile Gln Ala Gly His Ile Trp Ile Gly Tyr Asn
435                 440                 445

Ala Tyr Asn Gly Asn Arg Val Tyr Cys Pro Val Arg Thr Cys Gln Gly
450                 455                 460

Val Pro Pro Asn His Ile Pro Gly Val Ala Trp Gly Val Phe Lys
465                 470                 475                 480

485                 490                 495

<210> SEQ ID NO 2
<211> LENGTH: 495
<212> TYPE: PRT
<213> ORGANISM: Artificial sequence
<220> FEATURE:
<223> OTHER INFORMATION: synthetic sequence

<400> SEQUENCE: 2

```
Met Ala Lys Thr Gln Ala Glu Ile Asn Lys Arg Leu Asp Tyr Ala
1               5                   10                  15

Lys Gly Thr Val Asp Ser Pro Tyr Arg Val Lys Lys Ala Thr Ser Tyr
                20                  25                  30

Asp Pro Ser Phe Gly Val Met Glu Ala Gly Ala Ile Asp Ala Asp Gly
            35                  40                  45

Tyr Tyr His Ala Gln Cys Gln Asp Leu Ile Thr Asp Tyr Val Leu Trp
        50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Glu Gln Trp Gly His Ile Gly Ile Val Tyr Asp Gly Gly Asn Thr Ser
        115                 120                 125

Thr Phe Thr Ile Leu Glu Gln Asn Trp Asn Gly Tyr Ala Asn Lys Lys
130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Ser Lys Thr Pro Ala Pro Lys Lys Ala Thr Leu Lys Val
            180                 185                 190

Ser Lys Asn His Ile Asn Tyr Thr Met Asp Lys Arg Gly Lys Lys Pro
        195                 200                 205

Glu Gly Met Val Ile His Asn Asp Ala Gly Arg Ser Ser Gly Gln Gln
        210                 215                 220

Tyr Glu Asn Ser Leu Ala Asn Ala Gly Tyr Ala Arg Tyr Ala Asn Gly
225                 230                 235                 240

Ile Ala His Tyr Tyr Gly Ser Glu Gly Tyr Val Trp Glu Ala Ile Asp
                245                 250                 255

Ala Lys Asn Gln Ile Ala Trp His Thr Gly Asp Gly Thr Gly Ala Asn
            260                 265                 270

Ser Gly Asn Phe Arg Phe Ala Gly Ile Glu Val Cys Gln Ser Met Ser
        275                 280                 285

Ala Ser Asp Ala Gln Phe Leu Lys Asn Glu Gln Ala Val Phe Gln Phe
290                 295                 300

Thr Ala Glu Lys Phe Lys Glu Trp Gly Leu Thr Pro Asn Arg Lys Thr
305                 310                 315                 320

Val Arg Leu His Met Glu Phe Val Pro Thr Ala Cys Pro His Arg Ser
                325                 330                 335

Met Val Leu His Thr Gly Phe Asn Pro Val Thr Gln Gly Arg Pro Ser
            340                 345                 350

Gln Ala Ile Met Asn Lys Leu Lys Asp Tyr Phe Ile Lys Gln Ile Lys
        355                 360                 365

Asn Tyr Met Asp Lys Gly Thr Ser Ser Thr Val Val Lys Asp Gly
370                 375                 380

Lys Thr Ser Ser Ala Ser Thr Pro Ala Thr Arg Pro Val Thr Gly Ser
385                 390                 395                 400
```

-continued

```
Trp Lys Lys Asn Gln Tyr Gly Thr Trp Tyr Lys Pro Glu Asn Ala Thr
                405                 410                 415

Phe Val Asn Gly Asn Gln Pro Ile Val Thr Arg Ile Gly Ser Pro Phe
            420                 425                 430

Leu Asn Ala Pro Val Gly Gly Asn Leu Pro Ala Gly Ala Thr Ile Val
        435                 440                 445

Tyr Asp Glu Val Cys Ile Gln Ala Gly His Ile Trp Ile Gly Tyr Asn
    450                 455                 460

Ala Tyr Asn Gly Asn Arg Val Tyr Cys Pro Val Arg Thr Cys Gln Gly
465                 470                 475                 480

Val Pro Pro Asn Gln Ile Pro Gly Val Ala Trp Gly Val Phe Lys
                485                 490                 495
```

COMPOSITION CAPABLE OF IMPROVING STABILITY OF BACTERIOPHAGE LYSIN PROTEINS

The present application is a 35 U.S.C. §371 submission of international application no. PCT/KR2012/004204 that was filed on 29 May 2012.

BACKGROUND OF THE INVENTION

1. Field of the Invention

The present invention relates to a composition for improving the stability of bacteriophage originated lysin proteins greatly even when the composition contains a high concentration of the bacteriophage originated lysin proteins. More precisely, the present invention relates to a method and a composition for improving significantly the stability of SAL-1 or LysK, the bacteriophage originated lysin protein, included at a high concentration in the composition.

2. Description of the Related Art

Since 1990s, the resistant bacteria showing the resistance against many antibiotics which had been widely used for the treatment of infectious diseases have been increased with causing problems. The most serious problem of them is the significantly lowered treatment effect of antibiotics in treating infectious diseases.

Therefore, it is an urgent request to develop a novel antibiotic substance that can overcome the said problem of resistance of the conventional antibiotics. The promising candidate for the novel antibiotic substance that draws our attention most is the bacteriophage originated lysin protein. This is called the bacteriophage lysin protein or lysin protein or lysin. The bacteriophage lysin protein is a kind of enzyme that is generated from the genetic information of a bacteriophage. The biological activity of the bacteriophage lysin protein, that is the enzymatic activity, is to destroy the peptidoglycan layer that is the major structure of bacterial cell wall. The bacteriophage lysin protein is mainly working in the course of destruction of bacterial cell wall. More precisely, when a bacteriophage is infected into a host, it is proliferated therein and the second generation bacteriophages are generated in the host bacteria. Then, the generated bacteriophages attempt to come out of the host bacteria through the cell wall, during which the bacteriophage lysin protein is working to destroy the cell wall (J. Bacteriol. 186: 4808-4812, 2004).

The bacteriophage lysin protein is naturally generated in the inside of bacteria from the genetic information of a bacteriophage, as explained hereinbefore, but is also synthesized by using recombinant protein technology and then applied to the bacterial cell wall in order to break the peptidoglycan layer. Because of this characteristics, the attempts to use the bacteriophage lysin protein as an antibacterial protein working against bacteria have been increased (U.S. Pat. No. 8,058,225; U.S. Pat. No. 8,105, 585). In particular, the attempt to use this protein as a treatment agent for infectious diseases caused by the resistant bacteria is focused on a different mode of action from that of the conventional antibiotics (Science 294: 2170-2172, 2001; Curr. Opin. Microbiol. 8: 480-487, 2005).

SAL-1 that has been developed by the present inventors is also one of the bacteriophage lysin proteins (Antimicrob. Agents Chemother. 55: 1764-1767, 2011). SAL-1 comprises the amino acid sequence represented by SEQ. ID. NO: 1 and has the bacteriolytic activity specific to *Staphylococcus aureus*. In particular, SAL-1 also displays the bacteriolytic activity against the antibiotic-resistant MRSA (methicillin-resistant *Staphylococcus aureus*) or VRSA (vancomycin-resistant *Staphylococcus aureus*). Thus, it can be used as a treatment agent for infectious diseases caused by MRSA or VRSA. The said MRSA and VRSA are the representative antibiotic-resistant bacteria and the number of death caused by the infection with these is very big world-widely.

SAL-1 is very similar to LysK having the amino acid sequence represented by SEQ. ID. NO: 2 and the difference is found only in three residues. However, the antibacterial activity of SAL-1 is almost double the activity of LysK (Antimicrob. Agents Chemother. 55: 1764-1767, 2011).

To use the bacteriophage lysin protein commercially, it needs to be prepared in the form of a high concentration formula. Particularly, when it is used as a medicine, a high concentration unit is advantageous for the administration and handling because when a unit contains a high concentration of the protein, the dosage can be reduced.

In the previous study, the present inventors found out that when the said SAL-1 and LysK were included in a solution at a high concentration, aggregation was observed over the time of storage and this aggregation was also accelerated by an external physical impact, suggesting that the stability of the solution was in question. That kind of disadvantage was not preferred for the industrial use of the lysin protein. To secure the stability during the storage and for safe handling, it was required to develop a method to provide the stability high enough to a composition even when it is prepared in a high concentration liquid form.

The present inventors have confirmed that the addition of calcium ions or magnesium ions to the lysin protein is effective in increasing the biological activity thereof. However, even though the addition of such divalent cations was effective in increasing the biological activity, it also caused the decrease of the stability of the lysin protein included in the liquid form composition. To use industrially the composition comprising these two lysin proteins at high concentrations as active ingredients, it is also requested to develop a method to secure the stability of the lysin protein in the presence of calcium or magnesium ions.

Numbers of research papers and patent documents have been cited in this invention, which are presented in the brackets. At this time, the cited papers and patent documents are included in this invention as a whole in order to describe the arts and spirits and scope of the present invention more clearly.

SUMMARY OF THE INVENTION

It is an object of the present invention to provide a method and a composition for improving the stability of SAL-1 or LysK, the bacteriophage lysin protein, included at a high concentration in the composition.

It is another object of the present invention to provide a method and a composition for improving the stability of SAL-1 or LysK, the bacteriophage lysin protein, included at a high concentration in the composition in the presence of calcium ions or magnesium ions.

To achieve the above objects, the present inventors first screened a surfactant which was believed to be effective in improving the stability of the lysin protein in a solution comprising SAL-1 or LysK at a high concentration, and as a result the inventors confirmed that poloxamer was very suitable for that purpose. Further, the present inventors confirmed that when the said poloxamer was added to a composition, SAl-1 or LysK was still stable even in the presence of magnesium ions or calcium ions, leading to the completion of the present invention.

Therefore, the present invention provides primarily a method and a composition for using the poloxamer as a stabilizer since the poloxamer was considered to be advantageous not only for preparing a solution comprising SAL-1 or LysK at a high concentration but also for maintaining the stability thereof in handling and for storage. The present invention also provides a method and a composition using the poloxamer as a stabilizer that is appropriate for preparing a solution comprising SAL-1 or LysK at a high concentration and additionally comprising magnesium ions or calcium ions for the purpose of improving the biological activity thereof and thus is advantageous for maintaining the stability in handling and storage thereof.

The calcium ions or magnesium ions herein can be added in various forms of salt. The type of salt herein is not limited, but chloride is preferred.

The concentration of calcium ions or magnesium ions herein is 0.1~20 mM, and more preferably 2~15 mM, and most preferably 10 mM.

The said poloxamer is a synthetic polymer surfactant, which is a nonionic copolymer composed of a central hydrophobic polyoxypropylene chain and two surrounding hydrophilic polyoxyethylene chains. The poloxamer was invented in 1973 (U.S. Pat. No. 3,740,421) and has been on the market under the brand-name of Pluronic. The diversity of the poloxamer is made by the length of the chain. There might be a light property change over the difference of the length but the basic property is all the same, suggesting that the basic effect is expected to be the same. Thus, the poloxamer herein is not limited, but poloxamer 188 (Pluronic F-68), that had been used as a pharmaceutical ingredient, is preferred.

The poloxamer content varies from the concentration of the lysin protein in a solution containing them. In general, the poloxamer concentration to give enough effect expected by the inventors is 0.01~2% (w/v), and preferably 0.1~0.5% (w/v).

The method of the present invention is not just effective in preparing a solution comprising a high concentration of the protein but also effective in preparing any other solutions comprising the protein at different concentrations. It is understood therefore that the effect of the present invention is more peculiar in a solution having a high concentration of the lysin protein. The expression "high concentration" in this invention is not limited in a specific standard but generally indicates at least 5 mg/ml and more preferably at least 10 mg/ml.

ADVANTAGEOUS EFFECT

To use industrially the bacteriophage originated antibacterial protein, SAL-1 or LysK, it is necessary to prepare a solution comprising the protein at a high concentration. If a solution comprising the protein at a high concentration can be prepared, it can be applied as a medicine, particularly an injectable solution, that is advantageous for reducing the dose of administration. However, in the course of the preparation of a solution comprising SAL-1 or LysK at a high concentration, the stability of the protein is decreased. According to the present invention, the stability of SAL-1 or LysK in a solution can be greatly improved, that is, according to the method and the composition of the present invention, a solution comprising SAL-1 or LysK at a high concentration can be easily prepared without worry of lowering the stability. The solution comprising SAL-1 or LysK at a high concentration, prepared according to the method of the invention, displays the greatly improved stability of the protein in a solution, indicating the handling and storage of the solution comprising the protein at a high concentration would be also worry-free. According to the present invention, there is no problem in adding calcium ions or magnesium ions to the solution in order to increase the biological activity of SAL-1 or LysK. In conclusion, the present invention provides a very stable composition comprising SAL-1 or LysK at a high concentration with securing the stability of the protein and the optimum biological activity of the same.

BRIEF DESCRIPTION OF THE DRAWINGS

The application of the preferred embodiments of the present invention is best understood with reference to the accompanying drawings, wherein:

FIG. 1 is a diagram illustrating the outline of the purification process of SAL-1 used in this invention.

DESCRIPTION OF THE PREFERRED EMBODIMENTS

Figure 2:
FIG. 2 is a set of photographs illustrating the process of the stability test performed in this invention.
Figure 3:
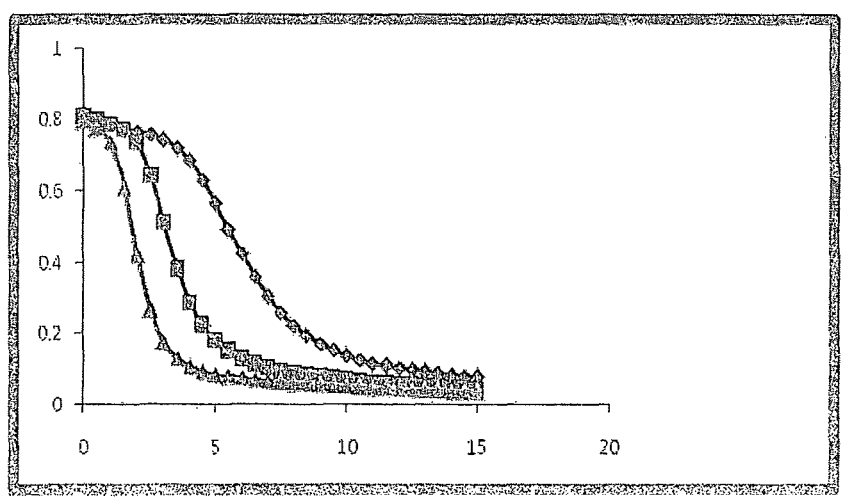
FIG. 3 is a graph illustrating the result of the biological activity test performed in this invention. The horizontal axis presents the analysis time (min.) and the vertical axis presents $OD_{600}$.
Figure 4:
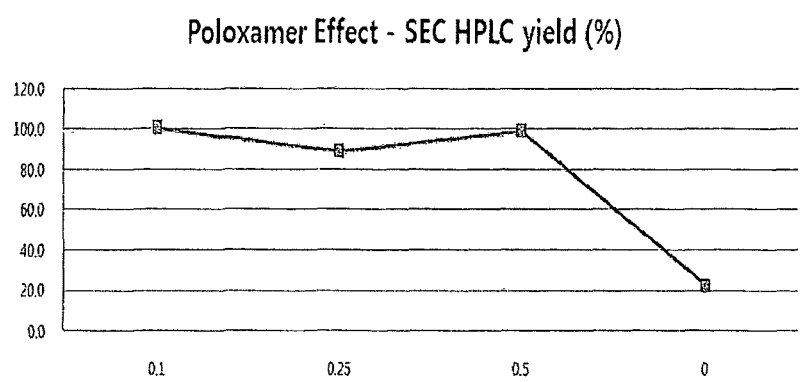
FIG. 4 is a graph illustrating the summary of the result of size exclusion liquid chromatography performed in order to analyze the effect according to the concentration of poloxamer. The horizontal axis presents the poloxamer content % (w/v), and the vertical axis presents the ratio (%) of the peak area of SAL-1 after stirring to the peak area of SAL-1 before stirring.
Figure 5:
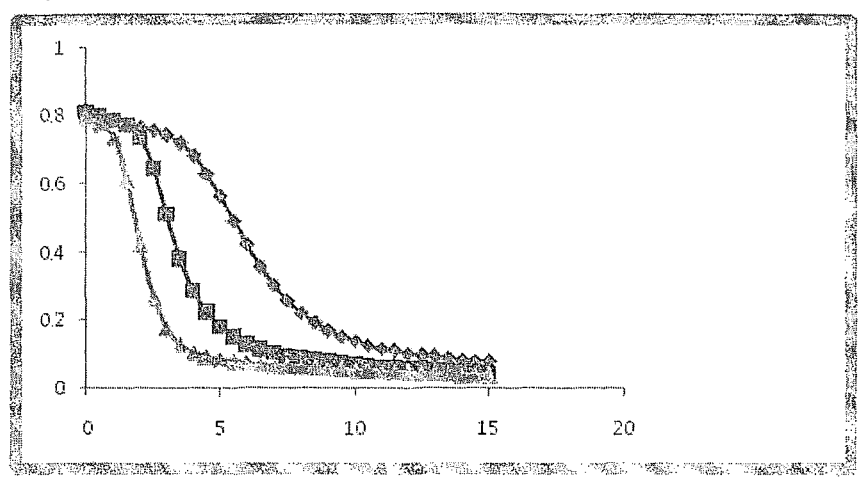
FIG. 5 is a graph illustrating the effect of the added magnesium ions or calcium ions to SAL-1 solution on the biological activity of SAL-1. The horizontal axis presents the analysis time (min.) and the vertical axis presents $OD_{600}$. Δ: calcium ions addition; □: magnesium ions addition; ◊: no addition.

As explained hereinbefore, the present invention provides a method and a composition characterized by containing poloxamer as a stabilizer to improve greatly the stability of the lysin protein in a solution comprising the bacteriophage lysin protein SAL-1 or LysK at a high concentration.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1

Investigation of a Surfactant Capable of Improving the Stability of a Solution Containing SAL-1

The SAL-1 used in this invention was prepared according to the method described in Korean Patent No 10-075998, particularly purified and prepared according to the method illustrated in FIG. 1. The elution fraction of SAL-1 showing at least 95% purity was finally selected and concentrated until the concentration reached 20 mg/ml, resulting in SAL-1 solution. The concentrated SAL-1 solution was replaced with different buffers. The buffers herein were L-Histidine buffer (10 mM L-Histidine, 5% (w/v) Sorbitol, pH 6.0), Tris-buffer (10 mM Tris-HCl, 140 mM NaCl, pH 7.5), Acetate buffer (10 mM Sodium acetate, 5% (w/v) Sorbitol, pH 5.0), Phosphate buffer A (10 mM Sodium phosphate, 5% (w/v) Sorbitol, pH 6.0), Phosphate buffer B (10 mM Sodium phosphate, 140 mM NaCl, pH 6.0), and HEPES buffer (10 mM HEPES, pH 7.3). The SAL-1 solution replaced with each buffer was added with different surfactants. Then, the proper surfactant was investigated. Selection of the proper surfactant was performed by investigating the increase of the stability of SAL-1 and also by measuring the decrease of the biological activity of SAL-1 as well. That is, a surfactant that was capable of increasing the stability of SAL-1 in a solution without reducing the biological activity of SAL-1 was screened. In this investigation, every surfactant could not all be tested, so those considered to be applicable for a pharmaceutical composition were targeted, which were exemplified by Polyoxyethylene nonylphenyl ether, Polysorbate 20, Polysorbate 40, Polysorbate 60, Tyloxapol, Sorbitan Monostearate, and Polyethyleneglycol Monostearate.

Stability test of the SAL-1 solution was performed as follows.

① adding a surfactant to SAL-1 solution (0.1%~0.5%);

② stirring the mixture at room temperature for 1 hour;

③ measuring turbidity at 600 nm using a spectrophotometer after stirring; and

④ judging the improvement of stability when the turbidity was least increased, compared with that before stirring.

Biological activity of SAL-1 was investigated as follows. Of course, those surfactants showing least stability improvement effect or none were eliminated from this investigation.

① adding a surfactant to SAL-1 solution (0.1% 0.5%);

② leaving the mixture at room temperature for 1 hour;

③ preparing a bacteria suspension comprising *Staphylococcus aureus* at the concentration of $8\times10^8$ cfu/ml by using 1×PBS (8 g/L NaCl, 0.2 g/L KCl, 1.44 g/L $Na_2HPO_4$, 0.24 g/L $KH_2PO_4$, pH 7.0);

④ adding the mixture of step ② to 1 ml of the bacteria suspension prepared in step ③ to make the concentration of SAL-1 therein to be 1 μg/ml (using the diluent of the mixture of step ②);

⑤ measuring $OD_{600}$ over the time by using a spectrophotometer (when bacteriolysis occurred by SAL-1, $OD_{600}$ was supposed to decrease over the time); and ⑥ judging the biological activity of SAL-1 as high when $OD_{600}$ was reduced greatly and fast over the time (judged by $TOD_{50}$, which means the $OD_{600}$ was reduced to half the first measured $OD_{600}$).

As a result, considering the stability of SAL-1 in a solution and the biological activity of SAL-1, poloxamer 188 was selected as the most appropriate surfactant that can improve the stability of SAL-1 in a solution with maintaining the biological activity of the same. Other surfactants were either weak in increasing the stability or reduced the biological activity of SAL-1. The stability test process according to the present invention is illustrated in FIG. 2. The biological activity test result is illustrated in FIG. 3. Buffer type did not affect the stability or the biological activity of SAL-1.

Example 2

Investigation of a Proper Concentration of Poloxamer

A proper concentration of poloxamer was investigated in this example. The stability and the biological activity of SAL-1 in a solution was investigated by the same manner as described in Example 1. To investigate the stability more accurately, size exclusion high performance liquid chromatography was also performed as follows. BioSep-SEC-S2000 column (7.8 mm×300 mm) was used as the analysis column. Buffer A (10 mM Tris-HCl, pH 7.5, 500 mM NaCl) was used as the analysis buffer. The flow rate after the addition of the sample was 1 ml/min. The volume of the sample added thereto was 50 μl, and the detection was performed using UV detector at 280 nm.

Following is the result of the investigation obtained by using a spectrophotometer when poloxamer was added at the concentrations of 0.1~0.5% (w/v). There was no significant difference over the concentration of poloxamer.

TABLE 1

| Poloxamer Content | $OD_{600}$ | |
|---|---|---|
| (%, w/v) | Stirring | Non-stirring |
| 0 | 1.2893 | 0.0008 |
| 0.10 | 0.0148 | −0.0004 |
| 0.25 | 0.0195 | −0.0003 |
| 0.50 | 0.0126 | 0.0003 |

The result of the size exclusion high performance liquid chromatography performed together is shown in FIG. 4. The result was consistent with that of the turbidity analysis using a spectrophotometer.

Based on the above results, the proper concentration of poloxamer was determined as 0.1% (w/v) to expect the full effect of it.

Example 3

Investigation of the Effect of Poloxamer Addition to the Composition Comprising Additionally Calcium Ions or Magnesium Ions It was previously confirmed that the addition of calcium ions or magnesium ions was effective in increasing the biological activity of SAL-1, unlike the addition of other ions (FIG. 5). Unfortunately the stability of SAL-1 in a solution comprising calcium ions or magnesium ions was reduced even though the biological activity of SAL-1 was increased by the said ions. Based on the fact, the present inventors wanted to find out whether or not the addition of poloxamer to SAL-1 solution could be effective in improving the stability of SAL-1 in the presence of calcium ions or magnesium ions. The stability test was performed by the same manner as described in Example 1. Since the kind of buffer did not affect the result, L-Histidine buffer (10 mM L-Histidine, 5% (w/v) Sorbitol, pH 6.0) alone was used as the buffer in this example. Calcium ions or magnesium ions were in the form of chloride herein and the concentration thereof was 10 mM. The concentration of poloxamer was 0.1% (w/v) as determined in Example 2. The result is as follows.

TABLE 2

| Addition | | | OD₆₀₀ after stirring |
|---|---|---|---|
| Calcium ions | Magnesium ions | Poloxamer | |
| × | × | × | 0.200 |
| × | ○ | × | 0.668 |
| ○ | × | × | 1.093 |
| × | × | ○ | 0.041 |
| × | ○ | ○ | 0.040 |
| ○ | × | ○ | 0.044 |

Example 4

Confirmation of the Effect of Poloxamer Addition in LysK Solution

The effect of poloxamer addition in LysK solution was also investigated by the same manner as described in Example 3. The LysK used in this example was prepared by the same manner as used for the preparation of SAL-1. Considering that the difference over the buffer was minor in Example 1, L-histidine buffer or Tris buffer (10 mM Tris-HCl, pH 7.0) was used to replace LysK solution (20 mg/ml), to which poloxamer was added at the concentration of 0.1% (w/v). As a result, the addition of poloxamer resulted in the significant increase of the stability of LysK, in both cases of using the above two buffers (data not shown).

Example 5

Investigation of the Long-Term Storage Stability

The stability that has been a target of the investigation in the above examples was the stability against external physical stimulus. In addition to the stability against physical stimulus, the storage stability is also very important for the industrial purpose. The SAL-1 solution prepared according to the present invention was kept in a refrigerator for 8 weeks, during which the stability of SAL-1 was investigated. Particularly, as shown in Example 2, size exclusion high performance liquid chromatography was performed for the stability analysis. The peak area presenting SAL-1 in the chromatography was analyzed to investigate the duration of SAL-1 peak over the time.

In this example, the concentrations of SAL-1 in the SAL-1 solution were 1 mg/ml, 13 mg/ml, and 20 mg/ml. The purpose of using different concentration was to find out what concentration of SAL-1 would be appropriate for the best effect of the present invention. The sample analysis was specifically performed 4 weeks later, 6 weeks later, and 8 weeks later, respectively.

Figure 6:
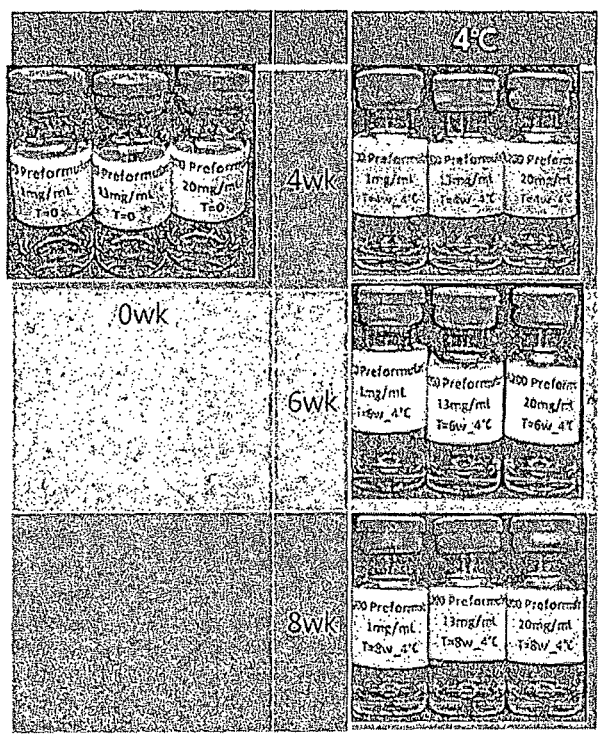
FIG. 6 illustrates the result of the stability test over the long-term storage of the SAL-1 solution prepared according to the present invention.

As a result, as shown in FIG. 6, the peak area was maintained at least 93% (chromatography peak area), compared with the early peak, in every concentration tested herein after the storage in a refrigerator. In the meantime, the peak area was only maintained 60% at best in the absence of poloxamer (data not shown).

The above results suggest that the composition of the present invention is effective in improving the stability of the lysin protein in the solution comprising the bacteriophage originated lysin protein as an active ingredient. In particular, the effect was high enough in a high concentration solution. The composition of the present invention has also been confirmed to be effective in the solution comprising particularly SAL-1 or LysK as an effective ingredient.

Those skilled in the art will appreciate that the conceptions and specific embodiments disclosed in the foregoing description may be readily utilized as a basis for modifying or designing, other embodiments for carrying out the same purposes of the present invention. Those skilled in the art will also appreciate that such equivalent embodiments do not depart from the spirit and scope of the invention as set forth in the appended Claims.

What is claimed is:

1. A method for stabilizing SAL-1 or LysK in a composition in solution comprising adding divalent cations to the solution of SAL-1 represented by SEQ. ID. NO: 1 or LysK represented by SEQ. ID. NO: 2, and adding poloxamer to the solution.

2. The method for stabilizing SAL-1 or LysK according to claim 1, wherein the divalent cations are calcium ions or magnesium ions or a mixture thereof.

3. The method for stabilizing SAL-1 or LysK according to claim 1, wherein the concentration of the divalent cations is 0.1 mM to about 20 mM.

4. The method for stabilizing SAL-1 or LysK according to claim 1, wherein the concentration of the poloxamer is 0.01% (w/v) to about 2% (w/v).

5. The method for stabilizing SAL-1 or LysK according to claim 1, wherein the poloxamer is poloxamer 188.

6. An antibiotic composition comprising the bacteriophage lysin protein SAL-1 represented by SEQ. ID. NO: 1 or LysK represented by SEQ. ID. NO: 2, divalent cations as activity enhancers, and poloxamer as a stabilizer.

7. The antibiotic composition according to claim 6, wherein the divalent cations are calcium ions, magnesium ions, or a mixture thereof.

8. The antibiotic composition according to claim 6, wherein the concentration of the divalent cations is 0.1 mM to about 20 mM.

9. The antibiotic composition according to claim 6, wherein the concentration of the poloxamer is 0.01% (w/v) to about 2% (w/v).

10. The antibiotic composition according to claim 6, wherein the poloxamer is poloxamer 188.

11. The method for stabilizing SAL-1 or LysK according to claim 2, wherein the concentration of the divalent cations is 0.1 mM to about 20 mM.

12. The method for stabilizing SAL-1 or LysK according to claim 4, wherein the poloxamer is poloxamer 188.

13. The antibiotic composition according to claim 7, wherein the concentration of the divalent cations is 0.1 mM is about 20 mM.

14. The antibiotic composition according to claim 9, wherein the poloxamer is poloxamer 188.

* * * * *